(12) United States Patent
Koyfman

(10) Patent No.: US 6,346,492 B1
(45) Date of Patent: Feb. 12, 2002

(54) FABRIC FOR USE IN PROSTHETICS

(75) Inventor: Ilya Koyfman, Ringoes, NJ (US)

(73) Assignee: American Medical Systems, Inc., Minnetonka, MN (US)

( * ) Notice: Subject to any disclaimer, the term of this patent is extended or adjusted under 35 U.S.C. 154(b) by 0 days.

(21) Appl. No.: 09/306,846

(22) Filed: May 6, 1999

(51) Int. Cl.$^7$ .................. D03D 15/00; D03D 15/08; D03D 17/00; D03D 23/00

(52) U.S. Cl. .................. 442/209; 442/182; 442/184; 442/199; 442/208; 442/212; 442/213; 442/216; 139/416; 139/421; 139/DIG. 1; 600/40; 623/11

(58) Field of Search ................ 442/182, 184, 442/199, 208, 209, 212, 213, 216; 139/416, 421, DIG. 1; 600/40; 623/11

(56) References Cited

U.S. PATENT DOCUMENTS

| 4,267,829 A | | 5/1981 | Burton et al. |
| 5,645,924 A | * | 7/1997 | Hamilton .................... 442/184 |
| 5,658,280 A | | 8/1997 | Issa |
| 5,702,387 A | | 12/1997 | Arts et al. |
| 5,810,764 A | | 9/1998 | Eggers et al. |

FOREIGN PATENT DOCUMENTS

| EP | 0 397 550 A2 | 11/1990 |
| WO | WO 92/03107 A | 3/1992 |

OTHER PUBLICATIONS

Description of Ultrex fabric and yarns.
AMS 700™ *Inflatable Penile Prosthesis Product Line, Inservice Script* brochure, American Medical Systems, 1992.
*Ultrex/Ultrex Plus* brochure, American Medical Systems, Inc., 1998.

* cited by examiner

Primary Examiner—Terrel Morris
Assistant Examiner—Norca L. Torres
(74) Attorney, Agent, or Firm—James W. Inskeep; Oppenheimer Wolff & Donnelly LLP

(57) ABSTRACT

A fabric used with an inflatable penile prosthesis and having a high fabric weave density is disclosed. The fabric is comprised of substantially non-distensible warp fibers and expandable/contractible fill fibers. The warp fibers are made of a 40 denier polyester yarn and the fill fibers are made of a 70 denier spandex yarn wrapped with a 40 denier polyester yarn. The fill fibers and warp fibers have sufficient fabric weave density so as to resist fabric distortion, such as fill separation. The fabric is assembled on the penile prosthesis so that the fill fibers circumscribe the girth of the prosthesis and the warp fibers extend along the length of the prosthesis

12 Claims, 3 Drawing Sheets

FABRIC FOR USE IN PROSTHETICS

FIELD OF THE INVENTION

The present invention relates generally to fabrics used with prosthetics and particularly relates to fabrics used with penile prostheses.

BACKGROUND OF THE INVENTION

Various types of penile prosthesis are currently available to cure or compensate for impotence, two of which include a non-inflatable, semi-rigid implantable prosthesis and an inflatable, implantable prosthesis. The non-inflatable, semi-rigid prosthesis is implanted within the corpora cavemosa of the penis and provides a generally constant erection. The inflatable prosthesis is also implanted in the corpora cavemosa but is connected to a hydraulic pumping device. The hydraulic pumping device is located within the patient's body and is used to inflate the prosthesis for erection and deflate the prosthesis for flaccidity.

Inflatable, implantable prostheses commonly include a cylindrically shaped pressure chamber made of silicone and a pump that is used to inflate or deflate the chamber. The chamber is encapsulated in a sleeve or sheath of biocompatible material (e.g. fabric) that constrains the expansion of the silicone pressure chamber.

One of the drawbacks occasionally observed with this type of inflatable prosthesis is the presence of weak spots in the sheath or fabric that surrounds the pressure chamber. Such weak spots are typically caused by separation in the texture of the fabric that can occur upon inflation of the chamber. Such separation can be particularly acute in the "hinge area" of the chamber. As a result, an aneurysm or bulge can develop in the pressure chamber extending into the separation in the fabric and the region where the pressure chamber folds on itself in the deflated condition, sometimes referred to as the "hinge region," thereby compromising the integrity and/or physical appearance of the prosthesis.

Therefore, it is desirable to provide a fabric for an implantable prosthetic and particularly an inflatable, implantable penile prosthesis that reduces the occurrence of or eliminates pressure chamber aneurysms without compromising the other advantageous attributes of the fabric, including tensile strength, fabric thickness or fabric width.

OBJECTS AND SUMMARY OF THE INVENTION

In view of the foregoing, it is an object of the present invention to overcome the deficiencies of existing fabrics used with inflatable, implantable prostheses.

It is a further object of the present invention to provide a penile prosthesis fabric that minimizes the occurrence of chamber aneurysms without compromising tensile strength, fabric thickness or fabric width.

It is a further object of the present invention to provide a penile prosthesis fabric with increased fabric weave density.

The present invention attempts to address these objects and other objects not specifically enumerated herein through the use of a fabric used with an implantable prosthesis comprising warp fibers made of a first denier one-ply yarn and fill fibers made of a second denier two-ply yarn having the ability to expand and contract, wherein the second denier is higher than the first denier. In addition, the number of warp fibers and fill fibers provide a high fabric weave density.

DETAILED DESCRIPTION

Figure 1:
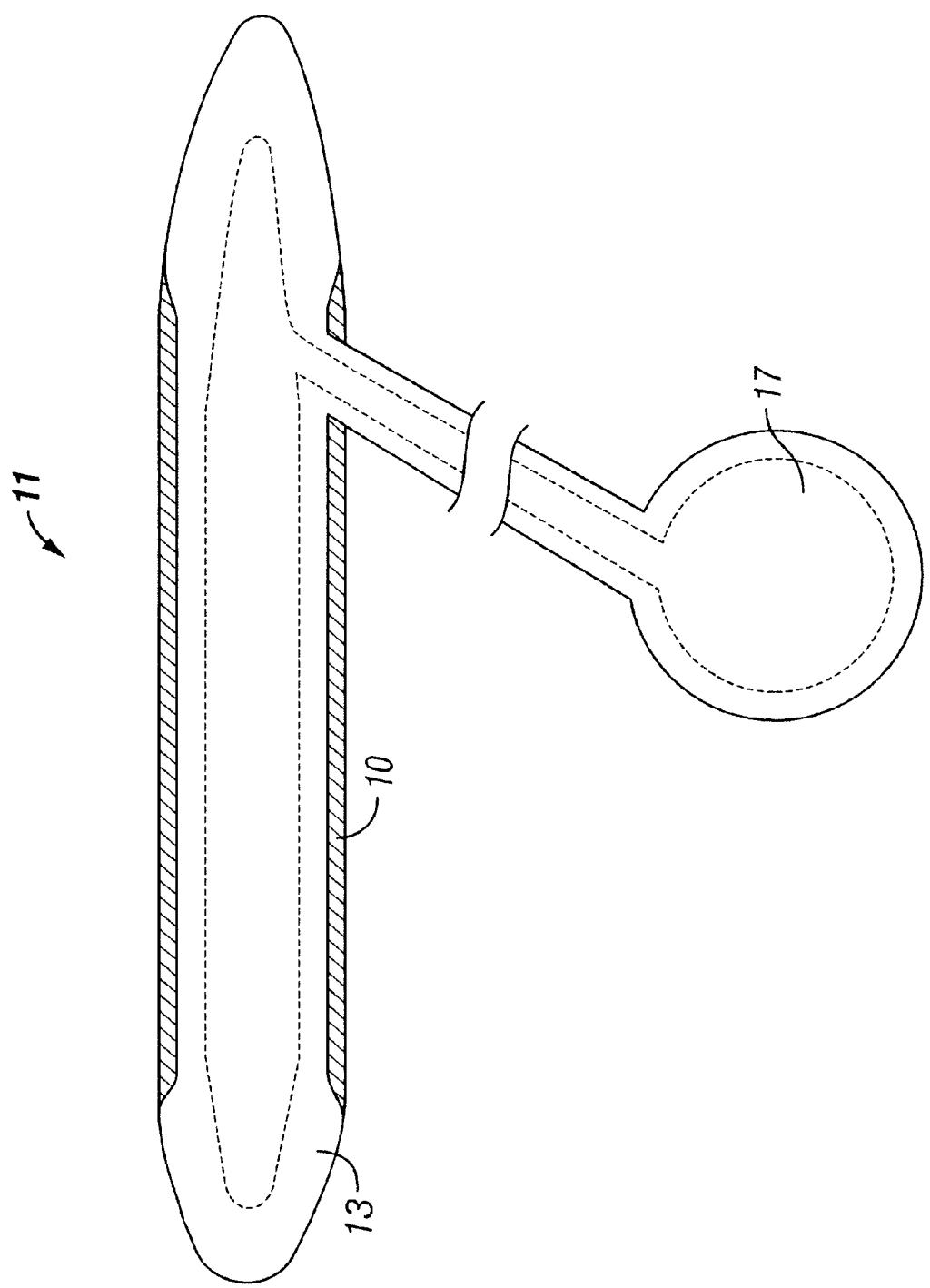
FIG. 1 is a cross-sectional view of a penile prosthesis covered in a fabric in accordance with a preferred embodiment of the present invention.

Referring to FIG. 1, an inflatable penile prosthesis 11 includes a cylindrically shaped pressure chamber 13, typically made of silicone, and a pump 17 used to inflate or deflate the chamber 13. The chamber 13 is covered in a sleeve or sheath of biocompatible fabric 10 that constrains the expansion of the silicone pressure chamber 13.

Figure 2:
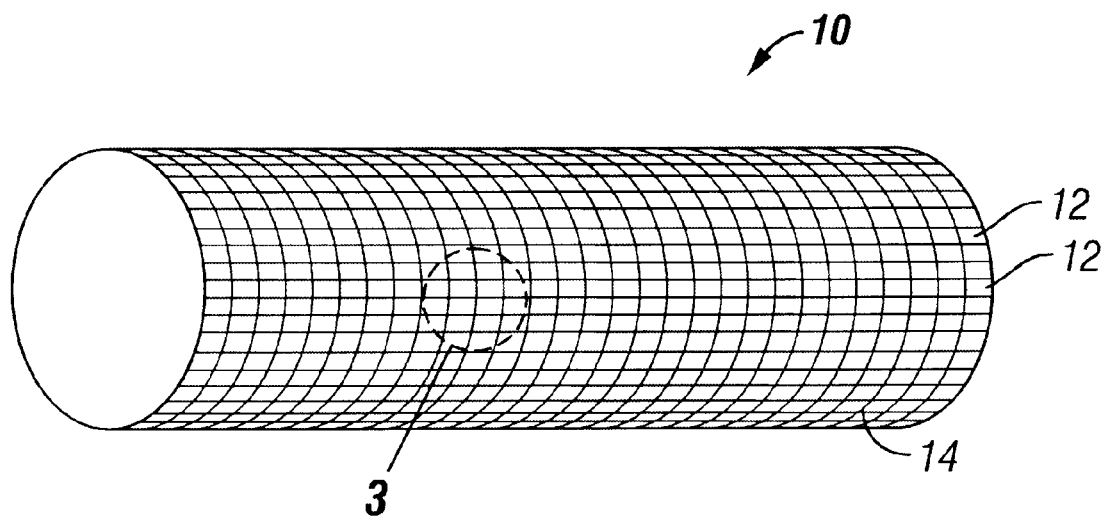
FIG. 2 is a perspective view of a prosthesis fabric in accordance with a preferred embodiment of the present invention.
Figure 3:
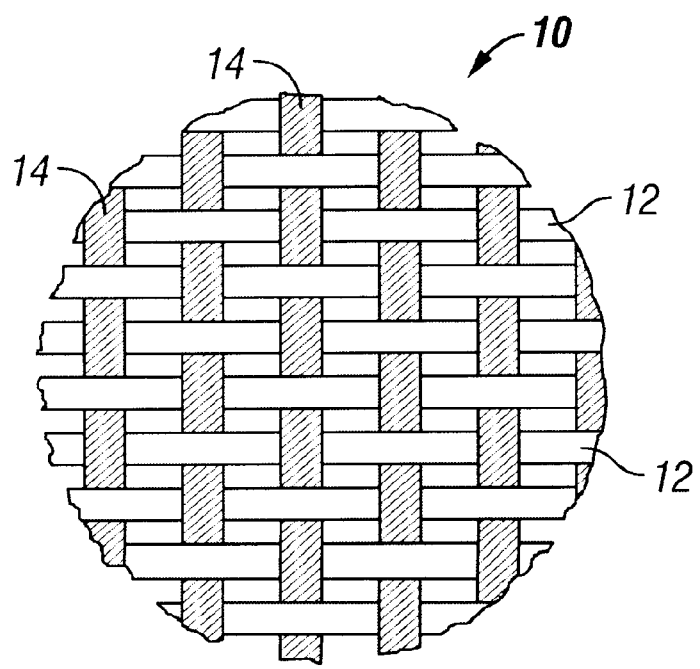
FIG. 3 is a perspective, partly enlarged view taken along section -3- of FIG. 1 of a prosthesis fabric in accordance with a preferred embodiment of the present invention.

An embodiment of a fabric 10 used with an inflatable penile prosthesis or other similar device in accordance with the present invention is shown in FIGS. 2 and 3. The fabric 10 is comprised of a weave of warp fibers 12 and pick or fill fibers 14. Fill fibers 14 are straight fibers that run along the width or circumference of the fabric 10. Warp fibers 12 are straight fibers that run in the length-wise direction of the fabric 10. As shown in FIG. 3, the warp fibers may be smaller relative to the fill fibers 14. In a preferred embodiment, the fabric 10 is applied to the penile prosthesis so that the fill fibers 14 circumscribe the girth of the prosthesis and the warp fibers 12 extend along the length of the prosthesis.

For use in an inflatable penile prosthesis, the fabric 10 must allow for repeated radial or girth expansion and contraction according to the intended use of the device. The fabric 10 must also provide, however, an evenly distributed constraint to the prosthetic so that the device does not inflate into an undesirable configuration. Accordingly, a combination of materials, typically spandex and polyester, are used as the warp and fill fibers 12,14. Spandex is the generic name for a synthetic fiber or yarn that offers durability and good stretch and abrasion resistance. Similar to spandex, polyester is also a synthetic yarn, and is commonly characterized by its quick drying time, high strength abrasion resistance, and crease resistance. In the context of a penile prosthesis, the spandex primarily provides the elasticity in the fabric 10 necessary for expansion of the prosthesis and the polyester primarily provides the structural integrity to the fabric 10.

Figure 4:
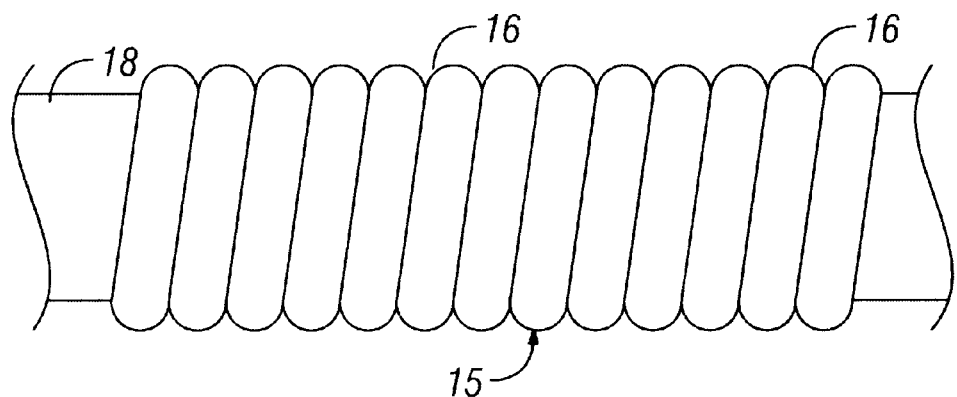
FIG. 4 is a perspective view of a strand used in a fabric in accordance with a preferred embodiment of the present invention.

Referring to FIG. 4, one element or covered yarn 15 of the fill fiber 14 used in a preferred embodiment is shown and includes a 40 denier polyester yarn 16 wrapped or coiled around a 70 denier spandex yarn 18. Denier is a measurement of fiber weight used to express the yield, or thickness, of a thread or yarn (e.g. 1 denier=1 gram per 9,000 meters). For example, a particular material of high denier, such as 70, would have larger fibers and stronger material characteristics than that same material of small denier, such as 40, which would have finer fibers and lesser yields.

The amount of expansion of the covered yarn 15 is directed by the number of turns of polyester yarn 16 per inch of spandex yarn 18 (termed "turns per inch" or tpi). For example, a covered yarn 15 having 6 tpi would have more constrained expansion than a covered yarn 15 having 20 tpi. The covered yarn 15 of the present invention has approximately 19–25 tpi, and preferably has 22 tpi.

Figure 5:
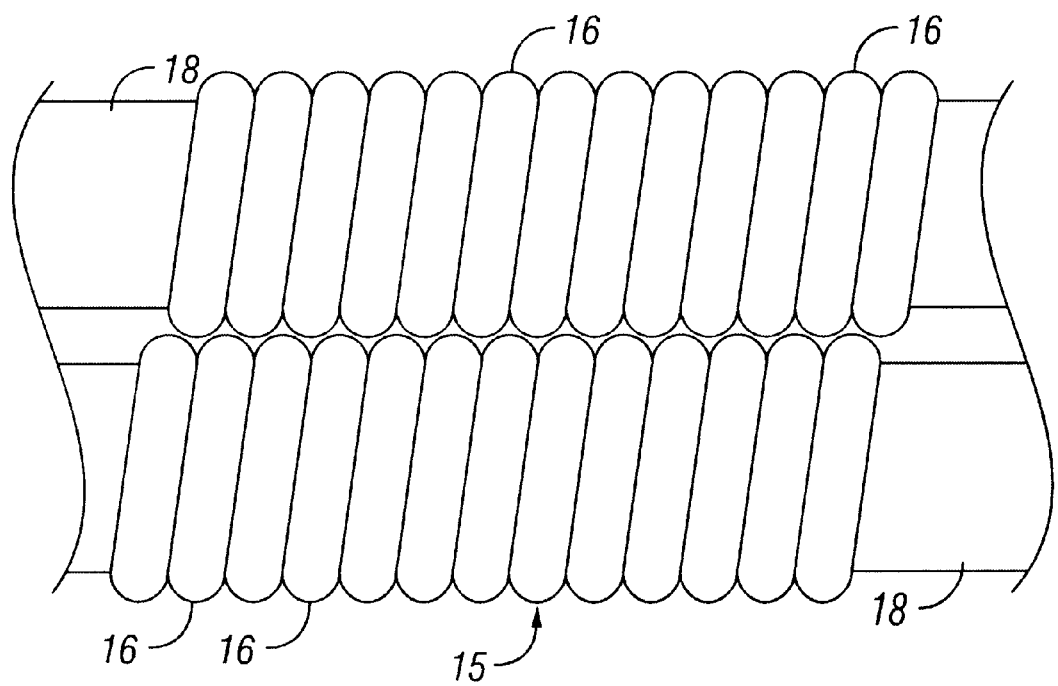
FIG. 5 is a perspective view of a two-ply fiber used in a fabric in accordance with a preferred embodiment of the present invention

As shown in FIG. 5, the fill fiber 14 used in a preferred embodiment includes two covered yarns 15 which are positioned parallel to each other. The fill fiber 14 may be characterized as a two-ply fiber insofar as it uses two covered yarns 15.

Referring to FIG. 3, the warp fibers 12 of a preferred embodiment are made of a 40 denier polyester yarn 16. The relatively non-distensible polyester yarns 16 that comprise the warp fibers 12 limit or, in certain embodiments, even prevent elongation of the woven fabric 10 and, thus, also prevent elongation of the penile prosthesis along its axis. The denier of the warp fibers 12 also provide, however, sufficient density so that the longitudinal tensile strength of the fabric 10 is not compromised during inflation of the prosthesis.

In view of the above, it is evident that a preferred embodiment of the present invention provides a biocompatible fabric 10 having anisotropic properties such that the fill fibers 14 and warp fibers 12 of the fabric 10 allow for radial expansion, but substantially prevent longitudinal expansion, when assembled on a penile prosthesis.

The particular fill fibers 14 and warp fibers 12 comprising the fabric 10 of the present invention must be made of an appropriate material and have sufficient weight or denier so as to resist fabric distortion, such as fill separation. Although a preferred embodiment of the present invention includes a fill fiber 14 comprising two covered yarns 15 using a 70 denier spandex yarn 18 wrapped with a 40 denier polyester yarn 16 and a warp fiber 12 made of a 40 denier polyester yarn, other fiber weights and materials may also be used provided that the fiber configurations and materials provide for radial expansion yet sufficiently resist fabric 10 distortion.

Fiber weight or density can be decreased by texturizing the fibers via a heating process. Texturization is commonly used in the textile industry to provide greater thickness and increased flat width to fabrics. In addition, the use of texturization also improves the weaving process of the fabric to avoid a "terry-cloth" phenomenon. In a preferred embodiment of the present invention, the 40 denier polyester yarns 16 of the fill fibers 14 have been texturized to arrive at the desired fiber strength and density.

In addition to fiber weight or denier, adequate fabric weave density may also reduce the occurrence of fabric distortion. Fabric weave density is typically defined by the warp count and fill count of the fabric. For the fabric 10 of the present invention, the warp count may range from approximately 267 to 269 and is preferably 269. In addition, the fill count is preferably 68 picks per inch, but may be within the range of 66 to 68 picks per inch. The fabric weave density should be configured so as to provide sufficient fabric thickness and flat width without compromising the structure or function of the penile prosthesis.

The particular fiber characteristics and weave density of the fabric 10 of the present invention provide a smooth, pattern-free material. Due to its pattern-free surface, the fabric 10 is less susceptible to material distortions, such as fill separation. Further, the distinct fiber characteristics of the fabric 10 allow the fabric 10 to repeatedly stretch and then return to its original shape without causing residual runs or creases in the fabric 10.

The foregoing description addresses embodiments encompassing the principles of the present invention. The embodiments may be changed, modified and/or implemented using various types of arrangements. Those skilled in the art will readily recognize various modifications and changes which may be made to the invention without strictly following the exemplary embodiments and applications illustrated and described herein, and without departing from the scope of the invention which is set forth in the following claims.

What is claimed is:

1. A fabric used with an inflatable penile prosthesis comprising:

warp fibers made of a small denier one-ply yarn that is substantially non-distensible;

fill fibers made of a high denier two-ply yarn having the ability to expand and contract; and a number of said warp fibers and said fill fibers to provide a high fabric weave density.

2. The fabric according to claim 1, wherein said warp fibers are 40 denier.

3. The fabric according to claim 1, wherein said fill fibers are 70/40 denier.

4. The fabric according to claim 1, wherein said fill fibers are made of a polyester yarn wrapped around a spandex yarn.

5. The fabric according to claim 4, wherein said polyester yarn is 40 denier.

6. The fabric according to claim 4, wherein said spandex yarn is 70 denier.

7. The fabric according to claim 4, wherein said polyester yarn is positioned parallel to said spandex yarn.

8. The fabric according to claim 1, wherein said warp fibers are made of a polyester yarn.

9. The fabric according to claim 8, wherein said polyester yarn is 40 denier.

10. The fabric according to claim 1, wherein said fill fibers are texturized.

11. The fabric according to claim 1, wherein said number of fill fibers is 68 picks per inch.

12. The fabric according to claim 1, wherein said number of warp fibers is 269.

* * * * *